(12) United States Patent
Schoonover et al.

(10) Patent No.: US 9,671,349 B2
(45) Date of Patent: Jun. 6, 2017

(54) METHOD AND APPARATUS TO VERIFY CORRECT REPLACEMENT FLUID IN A THERAPEUTIC EXCHANGE PROCEDURE

(71) Applicant: FENWAL, INC., Lake Zurich, IL (US)

(72) Inventors: Matthew Schoonover, Palatine, IL (US); Lan T. Nguyen, Vernon Hills, IL (US); David Stude, Barrington, IL (US); Elizabeth Nelson, St. Cloud, MN (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 14/068,241

(22) Filed: Oct. 31, 2013

(65) Prior Publication Data

US 2015/0115180 A1    Apr. 30, 2015

(51) Int. Cl.
| | | |
|---|---|---|
| *G01N 21/00* | (2006.01) | |
| *G01N 21/84* | (2006.01) | |
| *G01N 33/487* | (2006.01) | |
| *G01N 33/49* | (2006.01) | |
| *A61M 1/34* | (2006.01) | |

(52) U.S. Cl.
CPC ............ *G01N 21/84* (2013.01); *A61M 1/342* (2013.01); *A61M 1/3437* (2014.02); *A61M 1/3455* (2013.01); *A61M 1/3496* (2013.01); *G01N 33/487* (2013.01); *G01N 33/49* (2013.01); *A61M 2205/18* (2013.01); *A61M 2205/27* (2013.01); *A61M 2205/3306* (2013.01); *A61M 2205/60* (2013.01); *A61M 2205/6009* (2013.01)

(58) Field of Classification Search
CPC ...................... A61M 2205/14; A61M 2205/18
USPC .................................................. 250/573–577
See application file for complete search history.

(56) References Cited

U.S. PATENT DOCUMENTS

| | | | | |
|---|---|---|---|---|
| 2009/0131861 | A1* | 5/2009 | Braig | ............... A61B 5/1427 604/66 |
| 2010/0282834 | A1* | 11/2010 | Devergne et al. | ............ 235/375 |
| 2010/0315231 | A1 | 12/2010 | Rada | |

(Continued)

FOREIGN PATENT DOCUMENTS

EP    2730305 A1    5/2014

OTHER PUBLICATIONS

European Patent Office, European Search Report, dated Feb. 27, 2015, Application No./Patent No. 14181190.1-1651, Applicant: Fenwal, Inc., 9 pages.

*Primary Examiner* — Thanh Luu
(74) *Attorney, Agent, or Firm* — Cook Alex Ltd.

(57) ABSTRACT

A method and apparatus are provided for automatically detecting the type of replacement fluid loaded by the operator during a therapeutic exchange procedure and to provide a warning alarm if an incorrect fluid is used. After the operator connects the container of replacement fluid to the replacement fluid line of a single-use kit and enters into the controller an identification of the exchange procedure to be performed, the replacement fluid is flowed through a segment of the kit in proximity to a sensor associated with the hardware component that detects the type of fluid flowing through the segment. The controller verifies whether the replacement fluid detected in the segment corresponds to that appropriate for the selected exchange procedure, and notifies the operator in the event that an incorrect replacement fluid has been loaded.

14 Claims, 5 Drawing Sheets

(56) References Cited

U.S. PATENT DOCUMENTS

| | | | |
|---|---|---|---|
| 2011/0009817 A1* | 1/2011 | Bennett | A61M 5/168 604/93.01 |
| 2013/0062404 A1 | 3/2013 | Devergne et al. | |
| 2013/0218123 A1 | 8/2013 | Beiriger | |

* cited by examiner

METHOD AND APPARATUS TO VERIFY CORRECT REPLACEMENT FLUID IN A THERAPEUTIC EXCHANGE PROCEDURE

FIELD OF THE DISCLOSURE

The present disclosure relates to apheresis procedures and, more particularly, to therapeutic apheresis procedures utilizing a durable separation device and single-use kit and in which blood is withdrawn from a patient and a replacement fluid is transfused to the patient.

BACKGROUND

When performing a therapeutic exchange procedure, blood is withdrawn from a patient, a portion comprising abnormal, pathogenic components is separated and retained, and the remaining components are transfused to the patient along with a replacement fluid. For example, in a therapeutic plasma exchange procedure (used for treating immune-mediated diseases, neoplasia, infectious diseases, sepsis, etc.), the replacement fluid may be saline or a solution containing albumin or fresh frozen plasma. In a therapeutic red blood cell exchange (used for treating sickle cell disease), the replacement fluid includes red blood cells originating from a healthy donor. In any event, it is important that the correct replacement fluid for the exchange procedure being performed be infused into the patient.

In performing a therapeutic exchange procedure, a single-use kit is used in connection with a hardware component including a durable separation device and programmable controller to separate the patient's blood. In current practices, the operator connects one or more containers of replacement fluid to the single-use kit as part of loading the kit onto the hardware component and relies solely on the operator's experience and training to ensure that the correct replacement fluid for the desired therapeutic exchange procedure is selected. Because of the potential for significant adverse consequences in the event that an incorrect replacement fluid is loaded onto the system, it is desirable that the system automatically detect the type of replacement fluid loaded by the operator and provide a warning in the event an incorrect replacement fluid was connected.

SUMMARY OF THE DISCLOSURE

The present subject matter has a number of aspects which may be used in various combinations, and a disclosure of one or more specific embodiments is for the purpose of disclosure and description, and not limitation. This summary highlights only a few of the aspects of this subject matter, and additional aspects are disclosed in the drawings and the more detailed description that follows.

By way of the present disclosure, a method is provided for automatically detecting the type of replacement fluid loaded by the operator during a therapeutic exchange procedure and to provide a warning alarm if an incorrect fluid is used.

More particularly, a method and apparatus are provided for determining the identity of the replacement fluid which utilizes a reusable hardware component and a single-use kit. The kit comprises an inlet line, separation chamber, a replacement fluid line to which a container of replacement fluid is connected, and a return line, while the hardware component comprises a durable separation device and a programmable controller including a user interface. The operator connects the container of replacement fluid to the replacement fluid line, loads the replacement fluid container onto the durable separation device, and enters into the controller an identification of the exchange procedure to be performed. The controller automatically identifies the appropriate replacement fluid for the selected therapeutic exchange procedure. The replacement fluid is flowed through a segment of the kit in proximity to a sensor associated with the durable separation device that detects the type of fluid flowing through the segment. The controller verifies whether the replacement fluid detected in the segment corresponds to that appropriate for the selected exchange procedure, and notifies the operator in the event that an incorrect replacement fluid has been loaded.

In a first aspect of the disclosure, the method comprises: entering into the controller an identification of the therapeutic exchange procedure to be performed; automatically identifying the proper replacement fluid to be used for the identified therapeutic exchange procedure; loading a container of replacement fluid onto the hardware component so that the hardware component determines the identification of the replacement fluid in the container and provides a signal to the controller indicative of the determination; comparing the identification of the replacement fluid in the container to the proper replacement fluid for the identified therapeutic procedure to determine whether there is a match; and permitting further automatic operation of the system to perform the identified therapeutic only if there is a match.

In a further related aspect of the disclosure, the method comprises the determining of the identification of the replacement fluid in the container is based on the optical properties of the fluid.

In another related aspect of the disclosure, the method comprises the system providing a notice perceivable by the operator in the event that the identification of the replacement fluid in the container and the proper replacement fluid for the identified therapeutic procedure do not match. The notice may comprise a visual notice and/or an audible notice.

In a second aspect of the disclosure, an apparatus for performing a therapeutic fluid exchange procedure is provided comprising a hardware component, a single use kit and a controller with a user interface for enabling setting of parameters pertinent to the therapeutic exchange procedure to be performed by the apparatus. The controller is programmed for executing the following steps in response to an operator entering into the user interface an identification of the therapeutic exchange procedure to be performed: automatically identifying the proper replacement fluid to be used for the identified therapeutic exchange procedure; determining the identification of the replacement fluid in a container of replacement fluid loaded onto the hardware component based on a signal sent by the hardware component to the controller; comparing the identification of the replacement fluid in the container to the replacement fluid identified by the controller for the therapeutic procedure to be performed to determine whether there is a match; and permitting further automatic operation of the system to perform the identified therapeutic exchange procedure only if there is a match.

In a related aspect, the hardware component comprises a sensor that generates a signal indicative of the determination of the identification of the replacement fluid in the container based on the optical properties of the fluid.

In a further related aspect, the apparatus may comprise an alarm for providing a notice perceivable by the operator in the event that the identification of the replacement fluid in the container and the proper replacement fluid for the identified therapeutic procedure do not match. The alarm may provide a visually-perceptible notice and/or an audibly-perceptible notice.

BRIEF DESCRIPTION OF THE DRAWINGS

These and other aspects of the present subject matter are described in the following detailed description and shown in the attached figures, in which.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
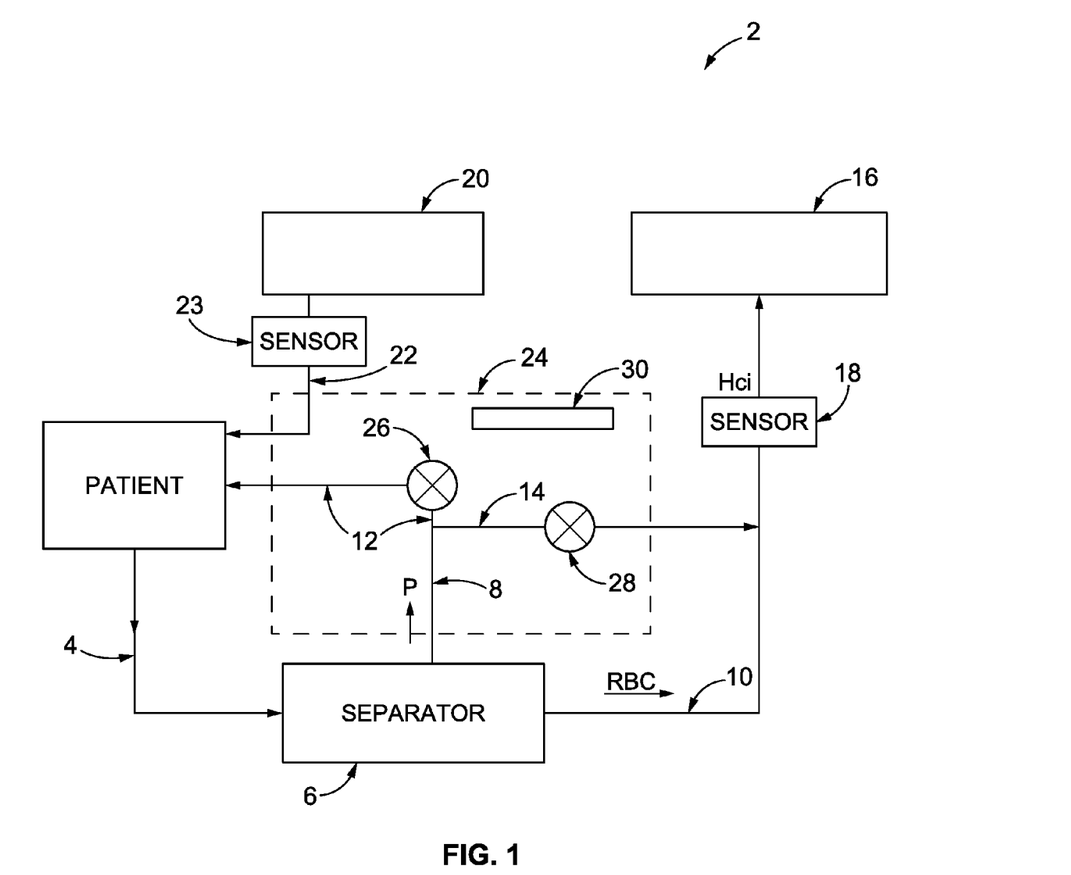
FIG. 1 is a diagrammatic view of a system for performing a method in accordance with one embodiment of the subject matter described herein.

In accordance with one embodiment of the present disclosure, FIG. 1 schematically illustrates a processing system, generally indicated at 2, that may be used for a therapeutic apheresis procedure in accordance with the subject matter described herein. The system 2 is particularly well suited to processing whole blood and/or other suspensions of biological fluids. By way of example and not limitation, the systems and methods described herein are particularly suited for a therapeutic red blood cell exchange and therapeutic plasma exchange procedures, during which the selected blood component is separated from the whole blood withdrawn from the patient and the remaining blood components, replacement cells and/or other replacement fluids, are returned to a patient. It is understood that the systems described herein are not limited to such collection and exchange procedures and that other procedures are also possible.

In FIG. 1, the system 2 includes a first flow path, generally indicated at 4, that communicates with a patient for flowing (withdrawing) at least a first fluid, such as whole blood, from the patient. In FIG. 1, a separator, generally indicated at 6, may be associated with the first flow path 4 for receiving the whole blood and separating the whole blood from the patient into one or more separated blood components. By way of example and in the context of a red blood cell exchange procedure, the separator 6 may separate primarily red blood cells from plasma and preferably separates red blood cells from the remaining blood components, e.g., plasma, platelets and white blood cells. In FIG. 1, a second or plasma flow path, generally indicated at 8, preferably communicates with the separator 6 for flowing the separated plasma and/or other remaining blood components, such as platelets and/or white blood cells, from the separator 6. A third or red blood cell flow path, generally indicated at 10, preferably communicates with the separator 6 for flowing the separated red blood cells from the separator.

The separated plasma may flow from the separator 6 generally in two ways or along two branches of the second flow path 8, such branches generally indicated at 12 and 14. A first branch 12 may communicate, either directly or indirectly with the patient and a second branch 14 may communicate with the red blood cell flow path 10 at a selected location to combine and/or mix with the separated red blood cells.

Also in FIG. 1, a first container or reservoir, generally indicated at 16, is preferably associated with the red blood cell flow path 10, such as at a downstream end of such flow path 10. The first reservoir 16 preferably communicates with the separator 6 to allow the separated red blood cells to flow from the separator 6 to such reservoir 16. A monitoring device, such as a sensor, generally indicated at 18, is optionally associated with the third flow path 10 at a sensing location that is preferably downstream of the selected location where separated plasma in flow path 14 and red blood cells in flow path 10 may combine.

In FIG. 1, a second reservoir, generally indicated at 20, may be associated with a source of a replacement fluid, such as fresh red blood cells, and may communicate with the patient, either directly or indirectly, by way of a replacement fluid flow path, generally indicated at 22. While only a single reservoir containing replacement fluid is shown in FIG. 1, the system may advantageously include additional reservoirs containing replacement fluid, as will be described in greater detail below. Although in FIG. 1, the replacement red blood cells flow to the patient separately from the separated plasma, it is also possible for the replacement red blood cells and separated plasma to flow by way of a combined flow path that communicates either directly or indirectly with the patient. In accordance with the present disclosure, the system also includes a sensor 23 for detecting the optical properties of the fluid as it flows through the flow path 22. The sensor 23 may be an optical sensor, such as an IR reflectance sensor, as is well known in the art. Alternatively, the sensor 23 may be a hematocrit sensor, such as that described in Muller et al. U.S. Pat. No. 6,419,822, incorporated herein by reference.

In FIG. 1, a controller or flow controller, generally indicated at 24, is preferably associated with one or more flow controlling devices, such as, for example, valves, generally indicated at 26 and 28, that preferably control the addition of the separated plasma to the separated red blood cells. In FIG. 1, such valves 26 and 28 are preferably respectively associated with the first and second branches 12 and 14 of the plasma flow path 8 for respectively controlling fluid flow of the separated plasma either to the patient or to the red blood cell flow path 10. By way of example, when the valve 26 is open and the valve 28 is closed, the separated plasma is directed to the patient. Alternatively, when the valve 26 is closed and the valve 28 is opened, the separated plasma is directed to the separated red blood cells in the red blood cells flow path 10. As a further alternative, the plasma flow path 8 may be provided with a pump (not shown in FIG. 1) to control the amount of plasma flowing to either the patient or to the red blood cell flow path 10. Other types of flow controlling devices may also be used as controllers, including but not limited to pumps, such as peristaltic or diaphragm pumps, as well as gravity-controlled flow controllers. The controller 24 may also be associated with the replacement fluid flow path 22 for controlling the fluid flow of the replacement fluid and may include various pumps, valves or other similar structures for controlling such flow.

In FIG. 1, such controller 24 may include a main controller, generally indicated at 30, such as a programmable controller employing a programmable microprocessor, that is operatively associated with the first and second valves 26 and 28 to control the fluid flow through each valve. In accordance with the present disclosure, the controller is programmed or configured to operate the system to perform a therapeutic exchange procedure, and to automatically verify the identity of the replacement fluid in container 20 and determine its suitability for the selected therapeutic exchange procedure, as set forth in greater detail below.

Figure 2:
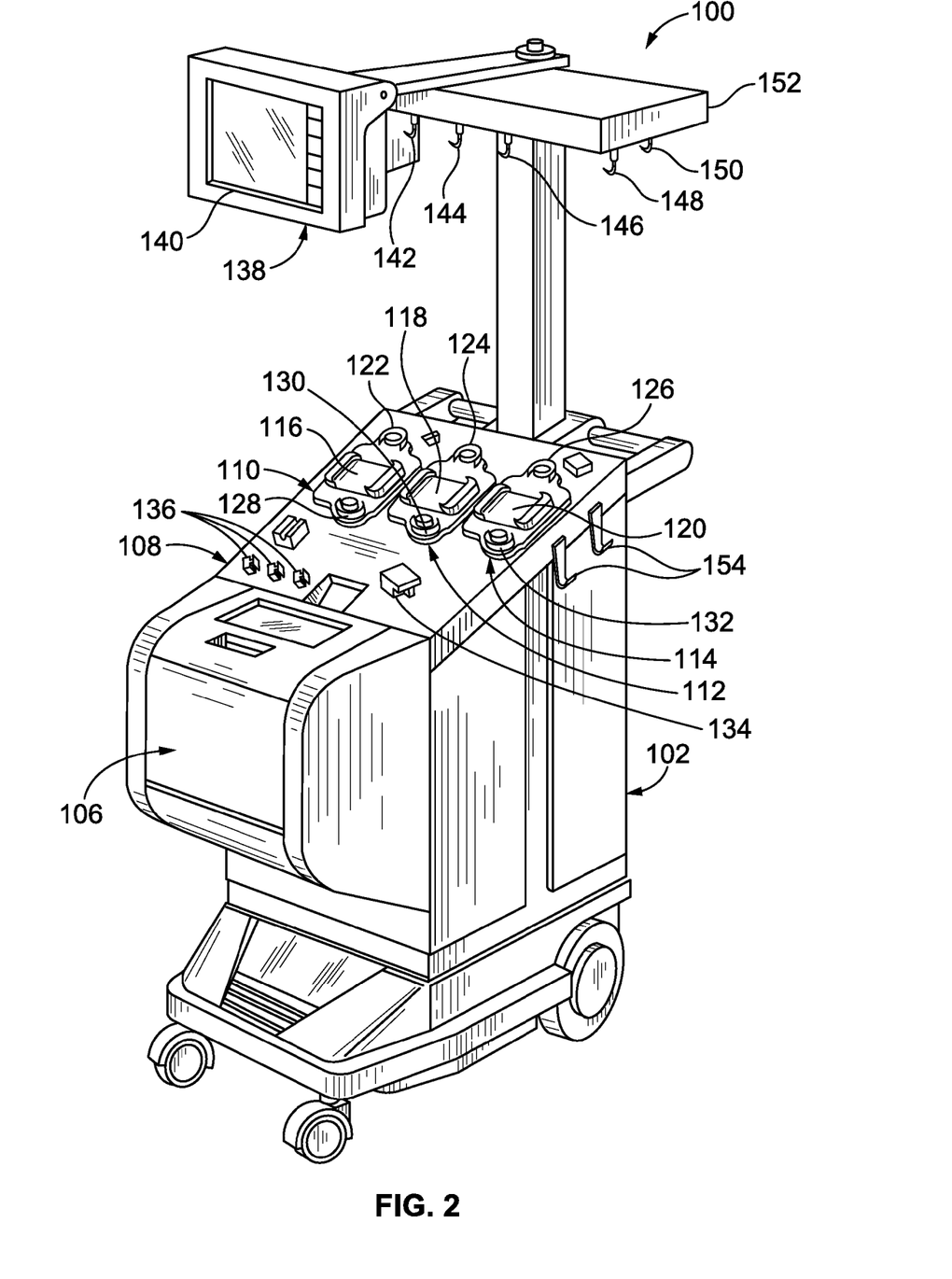
FIG. 2 is a perspective view of a reusable blood processing device that may be employed as part of or in association with the subject matter described herein.

FIG. 2 illustrates a centrifugal processing device, generally indicated at 100, that may be used for processing various fluids in accordance with the method and systems described herein. The illustrated embodiment is substantially identical to a commercial centrifuge sold by Fenwal, Inc. as the Amicus® separator, which is disclosed in numerous patents and patent applications, not limited to but including U.S. Pat. No. 5,868,696, to Giesler et al., issued Feb. 9, 1999, which is incorporated herein by reference.

As shown in FIG. 2, the centrifugal processing device 100 includes a separation assembly, specifically a centrifuge rotor assembly, generally within the housing indicated at 102, and is configured to control fluid flow through a disposable fluid processing set or kit, (generally indicated 104 in FIG. 3), used in association with the processing device 100. The separation assembly need not be a centrifugal processing assembly, and other separation technology or devices, such as membrane separators including spinning membrane separators, may also be used. The separation assembly 102 receives and separates a biological fluid, such as whole blood and/or other biological fluids, into two or more constituent components. The separation assembly 102 is preferably adapted to be durable and reusable over a long term. The fluid processing set 104, in contrast, is disposable, and a fresh sterile set is assembled with the separation assembly 102 for each use.

In FIG. 2, the separation assembly 102 includes an access compartment, generally indicated at 106, which houses a portion of the disposable set 104, such that when the separation assembly 102 is activated, the constituent components are separated within such portion of the set 104. A panel, generally indicated at 108, provides a surface for receiving another portion of the disposable set 104. For example, the panel 108 includes three pumping and valving stations, or respective left, middle and right stations, generally indicated at 110, 112 and 114, in FIG. 2, and each station 110, 112 and 114 respectively includes a valve interface portion 116, 118 and 120, that controls the opening and closing of associated valves in a disposable flow control cassette, described further below. Each station also has a respective upper flow controlling device or pump 122, 124, 126 and a lower flow controlling device or pump 128, 130, 132. Each illustrated pump 122, 124, 126, 128, 130, 132 is a peristaltic pump adapted to be associated with a section of tubing to provide flow control, although other types of pumps or other flow controlling devices, such as diaphragm pumps or gravity controlled devices are also possible. The panel 108 may further include one or more detectors 134, such as an optical detector, and/or other sensors or clamps, generally indicated at 136, for controlling and/or monitoring fluid and/or air flow in the disposable set 104.

As shown in FIG. 2, the system 100 further includes a controller, generally indicated at 138. The controller 138 is preferably a programmable controller that is operable to control the system 100 for various processes, as described in greater detail below. An operator interface module 140 may allow for viewing of the past, current and/or upcoming operations and/or provide for operator input by way of a touch screen and/or one or more tactile controls. One or more weight scales 142, 144, 146, 148, 150 may be associated with the controller 138. Such scales may be attached to a platform or stand 152 that allows one or more fluid containers to be attached to or hung from the scales and to allow for weight measurement of such containers during and/or after the processing procedure. One or more hooks 154 may also extend downwardly from a right or left side of the panel 108 to allow attachment of other fluid containers and may also be associated with a weight scale, if desired.

Figure 3:
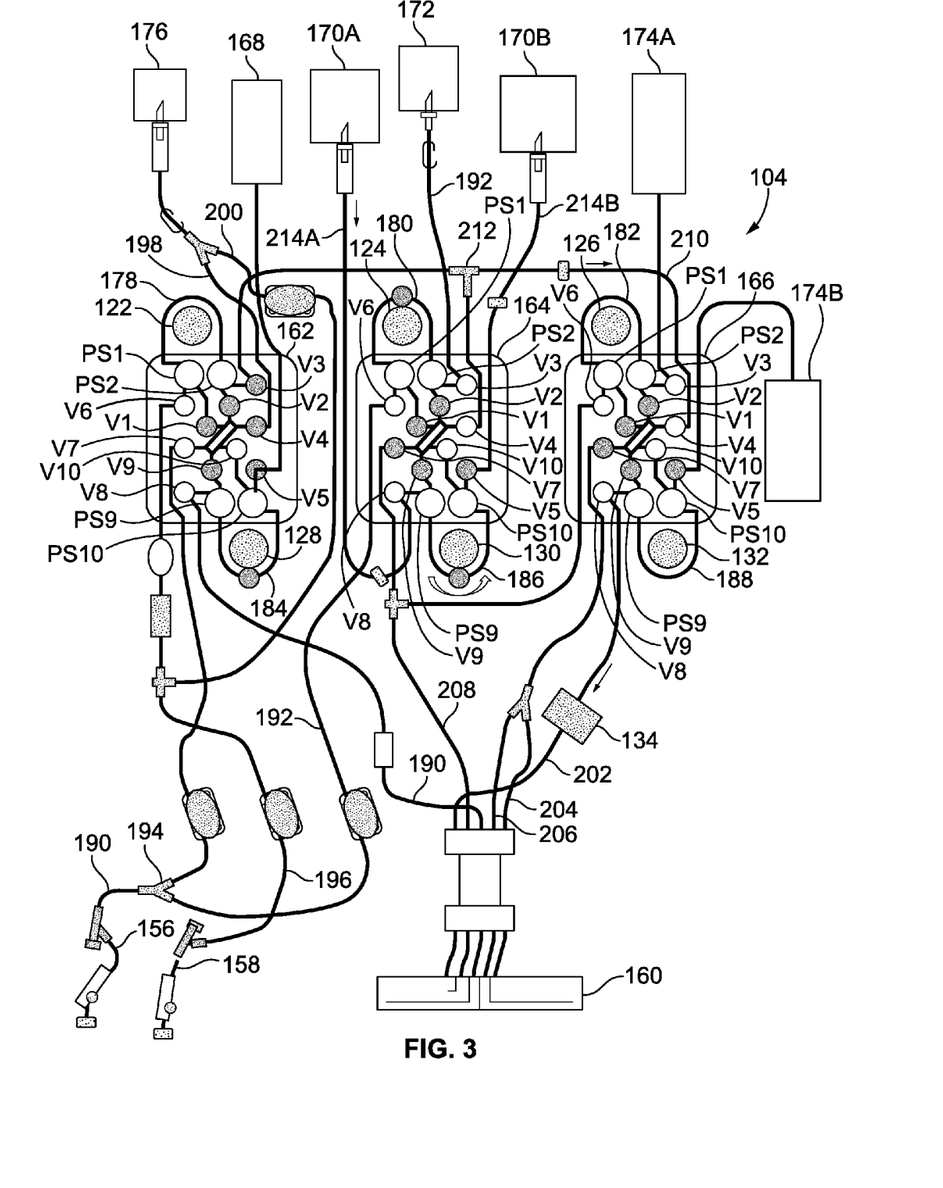
FIGS. 3 and 4 are plan views of a disposable tubing flow set for use with the processing device shown in FIG. 2, illustrating different modes of operation during a replacement fluid verification procedure in accordance with the present disclosure.
Figure 4:
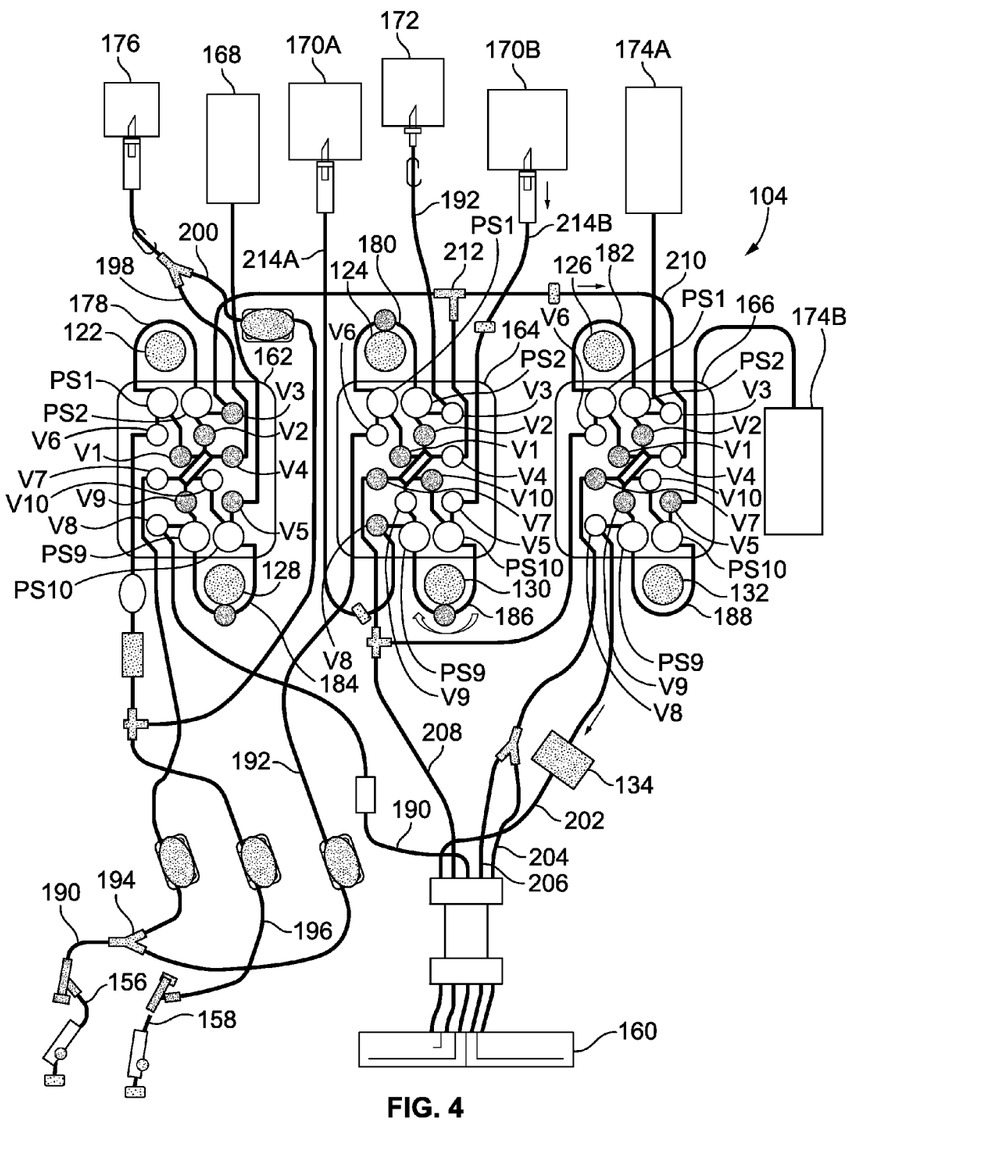

FIGS. 3 and 4 illustrate one possible disposable fluid processing set 104 that may be employed for use with a fluid separation device for performing a therapeutic exchange procedure in accordance with the present disclosure. The systems in FIGS. 3 and 4 include two sources of replacement fluid. FIGS. 3 and 4 differ from one another in that they illustrate the operation of the system for the verifying the loading of the correct replacement fluid for each of the two different sources.

The disposable set 104 is preferably adapted to be loaded onto a separation assembly, such as shown in FIG. 2 and disclosed in U.S. Pat. No. 5,868,696, incorporated by reference above, although other separation assemblies are also possible. The illustrated set 104 comprises a double needle processing set (with one needle for withdrawal of fluid from a patient and one needle for return of fluid to the patient), although the present disclosure is not limited to double needle processing and may include single needle and other types of processing sets.

The set 104 includes a draw tubing 156 and a return tubing 158 (each having a patient access device such as a needle and clamp 159 associated therewith), a processing chamber 160, left, middle and right pumping, flow control and valving cassettes 162, 164, 166, an auxiliary reservoir or container 168 for pressure relief or for diverted air, containers 170A, 170B for replacement fluids (such as saline, albumin, plasma, and/or replacement red blood cells), a container 172 for an anticoagulant, containers 174A and 174B for red blood cell waste, and a container 176 for saline. Each container 170A, 170B, 172, 174A, and 176 may be respectively associated with a corresponding weight scale (see, e.g., weight scales 142, 144, 146, 148, 150 shown in FIG. 2) for determining the amount of fluid that is removed from or added to such container. The set 104 also includes various tubing paths discussed in further detail below.

Each cassette 162, 164 and 166 has a similar internal construction and, as such, only one cassette 162 will be described. However, it is understood that like alpha-numeric reference characters used in connection with cassette 162 are also applicable to cassettes 164 and 166. The left cassette 162 includes at least one and preferably a plurality of pressure sensing chambers, such as PS01, PS02, PS09, and PS10, pre-formed fluid flow pathways, and at least one, and preferably a plurality of, valves, such as V1, V2, V3, V4, V5, V6, V7, V8, V9, and V10. The number and configuration of such chambers and valves are not limited to that shown, and other variations are also possible, including variations for the interconnecting flow paths between such chambers and valves. Each of the chambers and valves preferably is associated with a respective portion of the respective pumping and valving station 110, 112 and 114 (shown in FIG. 2) to control the flow of fluid.

As described above, each pump 122, 124, 126, 128, 130 and 132 may be a peristaltic pump adapted to be associated with a section of tubing to provide flow control. For example, each pump 122, 124, 126, 128, 130, and 132 may be associated with a respective tubing segment 178, 180, 182, 184, 186 and 188. The upper pumps 122, 124 and 126 are each associated with two pressure sensing chambers PS01 and PS02 with one being located downstream and the other located upstream of the pumps, depending on which direction is the desired flow direction, which direction may change, if desired, one or more times during and/or after the procedure. Similarly, the lower pumps 128, 130 and 132 are each associated with two pressure sensing chambers PS09 and PS10 located on either upstream or downstream side thereof. Such peristaltic pumps 122, 124, 126, 128, 130 and 132 are typically operated by rotation and include one or more outward extensions, rollers or the like that act on the exterior of the respective tubing segment 178, 180, 182, 184, 186 and 188 to progressively compress or "push" fluid in the desired direction of flow. In FIGS. 3 and 4, the pumps 124, 128 and 130 are shown with the pump rollers engaging the tubing, thus occluding the tubing and preventing flow therethrough unless the pump is operating.

The set 104 further includes a first flow path 190 in fluid communication with the draw tubing 156 for withdrawing whole blood from a patient. An anticoagulant flow path 192 may communicate with the first flow path 190 at a Y-branch connector 194 to allow anticoagulant to mix with the whole blood as it is withdrawn from the patient/donor. Anticoagulant from the anticoagulant container 172 may be pumped to the first flow path 190 by the upper or anticoagulant pump 124 of middle cassette 164 and flow through open valves V3 and V6 of such cassette to mix with the withdrawn whole blood. The set 104 includes a return or replacement fluid flow path 196 that fluidly communicates with the return tubing 158 to allow one or more fluids, such as a replacement fluid, to flow to the patient. One or more saline flow paths 198 and 200 may also be in respective communication with the whole blood and return flow paths 190 and 196 to allow saline flow, if desired, before, during and/or after the procedure.

Before turning to a discussion of the replacement fluid verification method that is the subject of the present disclosure, set forth below is a brief summary of a red blood cell exchange procedure, which is representative of the types of therapeutic exchange procedures with which the present verification method may be used. Thus, by way of example and not limitation, in a red blood cell exchange procedure, the withdrawn whole blood flows into the first flow path 190 and through the left cassette 162 and the lower or whole blood pump 128 of such cassette. The first flow path 190 preferably communicates with the processing chamber 160 so as to allow the withdrawn whole blood from the patient to be separated into selected constituent blood components, such as red blood cells, platelets and/or plasma.

Outlet flow paths 202 and 208 may allow separated blood components, such as red blood cells, plasma and/or platelets, to separately exit the processing chamber 160. For example, separated red blood cells from the processing chamber 160 may flow through a red blood cell path 208. Separated plasma from the processing chamber 160 may flow through the plasma flow path 202. An optical detector, such as the optical detector 134 discussed above, may be associated with the plasma flow path 202 to assist in optical detection of blood components, e.g. platelets or red cells, in the plasma constituent.

Separated red blood cells flowing from the processing chamber 160 preferably flow through the red blood cell flow path 208 to one of the red blood cell containers 174A or 174B. Separated red blood cells may flow through the right cassette 166 into one of the containers 174A or 174B. Separated plasma preferably is pumped by operation of the lower pump 132 of the right cassette 166. Such plasma pump 132 may be employed to determine the amount of plasma that is returned to the patient and the amount of plasma that flows out with the red blood cells in flow path 208. As discussed above, the removed red blood cell containers 174A, 174B may also be associated with weight scales for measuring the amount of the separated red blood cells flowing into such containers during the procedure.

The separated plasma from the processing chamber 160 flows through the plasma flow path 202 and is returned to the patient. For example, the separated plasma may flow from the processing chamber 160 through the right cassette 166 to a first passageway 210 in communication with the return flow path 196. Separated plasma is preferably pumped by the lower or plasma pump 132. Separated plasma may flow into the return flow path 196 at a selected location or connector 212, which combines the plasma and replacement fluid into a combined fluid stream for return to the patient. The amount of plasma returned to the patient depends on the desired ending hematocrit for the patient, the patient's hematocrit, and the hematocrit of the replacement fluid blood.

Replacement fluid flows from one of the replacement fluid containers 170A, 170B to the patient through the return flow path 196. For example, the replacement fluid flows from either container 170A (FIG. 3) or 170B (FIG. 4) through a replacement fluid source path 214A or 214B to the middle cassette 164. The lower or replacement pump 130 may assist the flow of the replacement fluid. The replacement fluid flows into the return flow path 196 and flows to the patient. A second optical detector 134 is associated with the plasma flow path 202 to assist in determining the optical properties of the replacement fluid. Preferably, the optical properties of the replacement fluid would be monitored continuously during an exchange procedure. However, in the illustrated system, the optical check of the replacement fluid is done at key transition points during the procedure, such as when the replacement fluid is first loaded onto the system or when changing from a non-cellular replacement fluid to a cellular replacement fluid.

As noted above, separated plasma may be combined with the replacement fluid in a single fluid stream. The return flow path 196 may also flow through the left cassette 162. A combined fluid stream may also be pumped by operation of the upper left or return pump 122 to assist the return flow to the patient. However, in a double needle procedure, the pump 122 is in a flow-through mode, and return blood flows through the open pathway.

Performance of the Method

Figure 5:
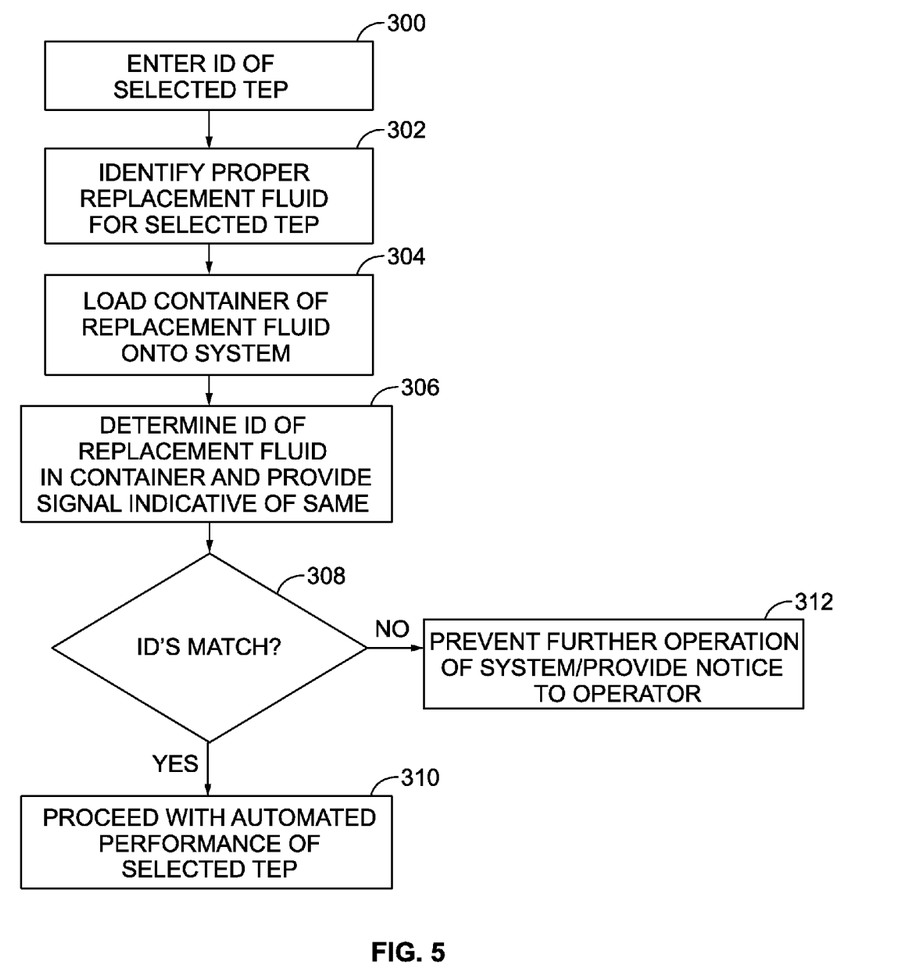
FIG. 5 is a flow chart setting forth a method for performing a replacement fluid verification procedure in accordance with the present disclosure.

The various steps of the method are shown in FIG. 5. It should be understood that the flow chart of FIG. 5 is exemplary, and that one or more of the steps may be modified or omitted, according to the requirements of the operator and patient.

In broad terms, in accordance with the present disclosure, a method is provided for automatically detecting the type of replacement fluid loaded by the operator during a therapeutic exchange procedure and to provide a warning alarm if an incorrect fluid is used.

The method utilizes a reusable hardware component and a single-use kit, as described in detail above. With reference to FIGS. 3 and 4, the kit 104 comprises an inlet line 156, separation chamber 160, a replacement fluid line, 214A or 214B to which a container of replacement fluid 170A or 170B is connected, and a return line 196. With reference to FIG. 2, the hardware component 100 comprises a durable separation device 102 and a programmable controller 130 including a user interface 138.

In performing the method, the operator connects the container of replacement fluid 170A and/or 170B to the replacement fluid line 214A and/or 214B, respectively. The replacement fluid container(s) are loaded onto the durable separation device 102, with the container(s) suspended from one of the weight scales 142, 144. The operator then enters into the user interface 140 of the controller 138 an identification of the exchange procedure to be performed. The controller 138 automatically identifies the appropriate replacement fluid for the selected therapeutic exchange procedure.

The replacement fluid is flowed through a segment of the kit in proximity to the optical sensor 134 associated with the durable separation device to determine the type of fluid flowing through the segment (based on the optical properties of the replacement fluid). More specifically, replacement fluid is flowed through cassette 164 and then cassette 166 by operation of the pump 130 (in a counter-clockwise direction for replacement fluid from container 170A (FIG. 3) or a clockwise direction for replacement fluid from container 170B (FIG. 4)), and then through flow path 202 past the sensor 134. The sensor 134 determines the identification of the replacement fluid (based on its optical properties), and sends a signal to the controller indicative of the same. The controller verifies whether the replacement fluid detected in the segment corresponds to that appropriate for the selected exchange procedure, and notifies the operator in the event that an incorrect replacement fluid has been loaded. The notice may comprise a visual and/or an audible alarm. In the event of an incorrect replacement fluid having been loaded, the controller may preclude further operation of the system.

The method is schematically illustrated in the flow chart of FIG. 5. With reference to FIG. 5, the method comprises: entering into the controller an identification of the therapeutic exchange procedure ("TEP") to be performed (Box 300); automatically identifying the proper replacement fluid to be used for the identified therapeutic exchange procedure (Box 302); loading a container of replacement fluid onto the hardware component (Box 304) so that the hardware component determines the identification of the replacement fluid in the container and provides a signal to the controller indicative of the determination (Box 306); comparing the identification of the replacement fluid in the container to the proper replacement fluid for the identified therapeutic procedure to determine whether there is a match (Box 308); and permitting further automatic operation of the system to perform the identified therapeutic only if there is a match (Box 310). If a match is not indicated, the system prevents further operation and informs the operator (Box 312).

As set forth above, the disclosed system and method have the following aspects.

In a first aspect of the disclosure, the method comprises: entering into the controller an identification of the therapeutic exchange procedure to be performed; automatically identifying the proper replacement fluid to be used for the identified therapeutic exchange procedure; loading a container of replacement fluid onto the hardware component so that the hardware component determines the identification of the replacement fluid in the container and provides a signal to the controller indicative of the determination; comparing the identification of the replacement fluid in the container to the proper replacement fluid for the identified therapeutic procedure to determine whether there is a match; and permitting further automatic operation of the system to perform the identified therapeutic only if there is a match.

In a further related aspect of the disclosure, the method comprises the determining of the identification of the replacement fluid in the container is based on the optical properties of the fluid.

In another related aspect of the disclosure, the method comprises the system providing a notice perceivable by the operator in the event that the identification of the replacement fluid in the container and the proper replacement fluid for the identified therapeutic procedure do not match. The notice may comprise a visual notice and/or an audible notice.

In a second aspect of the disclosure, an apparatus for performing a therapeutic fluid exchange procedure is provided comprising a hardware component, a single use kit and a controller with a user interface for enabling setting of parameters pertinent to the therapeutic exchange procedure to be performed by the apparatus. The controller is programmed for executing the following steps in response to an operator entering into the user interface an identification of the therapeutic exchange procedure to be performed: automatically identifying the proper replacement fluid to be used for the identified therapeutic exchange procedure; determining the identification of the replacement fluid in a container of replacement fluid loaded onto the hardware component based on a signal sent by the hardware component to the controller; comparing the identification of the replacement fluid in the container to the replacement fluid identified by the controller for the therapeutic procedure to be performed to determine whether there is a match; and permitting further automatic operation of the system to perform the identified therapeutic exchange procedure only if there is a match.

In a related aspect, the hardware component comprises a sensor that generates a signal indicative of the determination of the identification of the replacement fluid in the container based on the optical properties of the fluid.

In a further related aspect, the apparatus may comprise an alarm for providing a notice perceivable by the operator in the event that the identification of the replacement fluid in the container and the proper replacement fluid for the identified therapeutic procedure do not match. The alarm may provide a visually-perceptible notice and/or an audibly-perceptible notice.

Thus, this can be seen from the above description, the present disclosure has several different aspects which are not limited to the specific methods and apparatus shown in the attached drawings or described above. Variations of these concepts may be embodied in other steps for carrying out the methods and apparatus without departing from the scope of the disclosure.

The invention claimed is:

1. A method of performing a therapeutic blood component exchange procedure employing an automatic blood separating and processing device that includes a processor configured to be responsive to operator input of a selected one of a plurality of possible therapeutic blood component exchange procedures and to operate the blood separating and processing device to carry out of the selected exchange procedure, the method including:

flowing blood from a patient to the blood separating and processing device;

separating the blood into a plurality of blood components in a separator of the blood separating and processing device;

returning to the patient fewer than all of the withdrawn plurality of separated blood components, at least one of the separated blood components being withheld from return by the blood separating and processing device in accordance with the selected therapeutic blood component exchange procedure;

flowing to the patient a replacement fluid that is one of a cellular replacement fluid or a non-cellular replacement fluid;

during the flowing of a replacement fluid changing from the one of the cellular replacement fluid or a non-cellular replacement fluid to the other of the cellular replacement fluid or a non-cellular replacement fluid;

sensing the replacement fluid flowing to the patient;

comparing, at the time of changing, the sensed replacement fluid to the selected therapeutic blood component exchange procedure; and flowing the replacement fluid to the patient only if the processor determines that the sensed replacement fluid is a proper replacement fluid for the selected therapeutic procedure at the time of changing.

2. The method of claim 1 wherein the sensing of the replacement fluid is based on the optical properties of the fluid.

3. The method of claim 1 further comprising providing a notice perceivable by the operator in the event that the processor determines that the sensed replacement fluid is not the proper replacement fluid for the selected therapeutic blood component exchange.

4. The method of claim 3 wherein the notice comprises a visual notice and/or an audible notice.

5. The method of claim 1 wherein the selected therapeutic blood component exchange procedure is a red blood cell exchange procedure, and one of the replacement fluids comprises red blood cells.

6. The method of claim 1 wherein the selected therapeutic blood component exchange procedure is a therapeutic plasma exchange procedure, and one of the replacement fluids comprises one or more of saline, a solution containing albumin, or fresh frozen plasma.

7. The method of claim 1 wherein the sensing of the replacement fluid is performed continuously during the selected therapeutic blood component exchange procedure.

8. The method of claim 1 wherein the sensing of the replacement fluid is performed only at certain transition points during the selected therapeutic blood component exchange procedure.

9. An automatic blood separating and processing device for automatically performing a therapeutic blood component exchange procedure, the device including a blood separator and a processor configured to be responsive to operator input of a selected one of a plurality of possible therapeutic blood component exchange procedures and to operate the blood separating and processing device to carry out of the selected exchange procedure, including:

flowing blood from a patient to the blood separating and processing device;

separating the blood into a plurality of blood components in a separator of the blood separating and processing device;

returning to the patient fewer than all of the withdrawn plurality of separated blood components, at least one of the separated blood components being withheld from return by the blood separating and processing device in accordance with the selected therapeutic blood component exchange procedure;

flowing to the patient a replacement fluid that is one of a substantially cellular replacement fluid or a substantially non-cellular replacement fluid;

during the flowing of a replacement fluid changing from the one of the cellular replacement fluid or a non-cellular replacement fluid to the other of the cellular replacement fluid or a non-cellular replacement fluid;

sensing the replacement fluid flowing to the patient;

comparing, at the time of changing, the sensed replacement fluid to the selected therapeutic blood component exchange procedure; and flowing the replacement fluid to the patient only if the processor determines that the sensed replacement fluid is a proper replacement fluid for the selected therapeutic procedure at the time of changing.

10. The device of claim 9 wherein the device comprises a sensor that generates a signal indicative of the sensed replacement fluid based on the optical properties of the fluid.

11. The device of claim 9 further comprising an alarm for providing a notice perceivable by the operator in the event that the sensed replacement fluid is not the proper replacement fluid for the selected therapeutic blood component exchange procedure.

12. The apparatus of claim 11 wherein the alarm provides a visually-perceptible notice and/or an audibly-perceptible notice.

13. The device of claim 9 wherein the processor is configured to operate the device sense the replacement fluid continuously during the selected therapeutic blood component exchange procedure.

14. The device of claim 9 wherein the processor is configured to operate the device to sense the replacement fluid only at transition points during the selected therapeutic blood component exchange procedure.

* * * * *